United States Patent [19]
Bourgau et al.

[11] 3,931,290
[45] Jan. 6, 1976

[54] PREPARATION OF CARBOXYLIC ACID ALKYL ESTERS

[75] Inventors: Yolande Bourgau, Bron; Jean Berthoux, Decines; Ghislain Schwachhofer, Miribel, all of France

[73] Assignee: Rhone-Progil, Paris, France

[22] Filed: Sept. 8, 1972

[21] Appl. No.: 287,412

[30] Foreign Application Priority Data
Sept. 17, 1971 France .............................. 71.34327
Mar. 30, 1972 France .............................. 72.12000

[52] U.S. Cl. ...... 260/475 R; 260/476 R; 260/485 R; 260/493
[51] Int. Cl.² .......................................... C07C 67/04
[58] Field of Search ............ 260/493, 475 R, 476 R, 260/485 R

[56] References Cited
UNITED STATES PATENTS
2,021,852   5/1935   Coleman et al ...................... 260/493
FOREIGN PATENTS OR APPLICATIONS
916,772   1/1963   United Kingdom
2,024,948   1/1971   Germany OTHER PUBLICATIONS
Morrison et al., I, "Organic Chemistry," (1966) p. 511.
Morrison et al., II, "Organic Chemistry," (1966) pp. 732–733.
Hennis et al., "I & EC Product Research and Development," (1968) pp. 96–101.
Morrison et al., Organic Chemistry, 2nd Ed., (1966) pp. 511, 666, 668 & 721.
Gilman et al., Organic Chemistry, (1963) p. 751.

*Primary Examiner*—Lorraine A. Weinberger
*Assistant Examiner*—Michael Shippen
*Attorney, Agent, or Firm*—Browdy and Neimark

[57] ABSTRACT

Carboxylic acid alkyl esters are prepared by reacting an halo-alkane with an aqueous solution of an alkali metal salt of a carboxylic acid, using ammonia, a primary amine, a secondary amine, a heavy tertiary amine or a heavy quaternary ammonium salt as the catalyst.

10 Claims, No Drawings

PREPARATION OF CARBOXYLIC ACID ALKYL ESTERS

FIELD OF INVENTION

The present invention relates to carboxylic acid alkyl esters, and, more particularly, to a process for the preparation of carboxylic acid alkyl esters by reaction of an halo-alkane with an alkali metal salt of carboxylic acid in a hydro-organic medium in the presence of a catalytic amount of ammonia or its organic derivatives.

BACKGROUND OF INVENTION

It is known that carboxylic acid alkyl esters find numerous applications in solvent and polymer plasticizer fields. It is also known that it is possible to obtain fatty alcohols of great purity by saponification of such carboxylic alkyl esters. So it is very desirable to have a process for obtaining such esters in a very high yield, and this is especially so with esters, the alkyl chain of which is linear, because in this way one can obtain valuable linear fatty alcohols in high yields.

The reaction of an halo-alkane with an alkali metal salt of carboxylic acid, catalyzed by a light tertiary amine, such as triethylamine, has been described in French Pat. No. 1,357,888. But in this case the reaction medium constitutes an organic liquid phase, i.e. the halo-alkane, and a finely dispersed solid phase, i.e. the carboxylic acid alkali metal salt. However, this is an undesirable reaction medium because the alkali metal salt must be in the solid phase and not in the form of the much more convenient aqueous solution. Indeed, since the salt is most often obtained by salification in an aqueous medium of the corresponding acid by means of an alkaline base, the required use of the solid phase in the process of French Pat. No. 1,357,888 requires that the crude aqueous solution be subjected to expensive isolation operations such as solvent evaporation or atomization. Moreover, handling of the solid is much more difficult than handling the liquid, especially when operating continuously because the problems of material transport and stirring of liquids are greatly simplified compared to that of solids.

SUMMARY OF INVENTION

It is, accordingly, an object of the present invention to overcome the deficiencies of the prior art, such as indicated above.

It is another object of the present invention to provide a high yield reaction between an halo-alkane and an alkali metal salt of a carboxylic acid in aqueous medium to produce a carboxylic acid alkyl ester.

It is another object of the present invention to provide a method for producing carboxylic acid alkyl esters in high yields by the direct utilization of crude aqueous solutions of alkali metal salts of carboxylic acids.

It is another object of the present invention to provide for the reaction between an halo-alkane and an alkali metal salt of a carboxylic acid without the necessity of isolating the alkali metal salt of the carboxylic acid in the solid phase.

It is another object of the present invention to provide for the esterification reaction between an halo-alkane and an alkali metal salt of carboxylic acid in the presence of water.

These and other objects and the nature and advantages of the instant invention will be more apparent from the following description. In general, however, the present invention provides a substantial advance in the art because it permits the above-described esterification to be carried out in the presence of water.

The process of the present invention for preparing a carboxylic acid alkyl ester by reaction between an halo-alkane and an alkali metal salt of a carboxylic acid is particularly characterized by carrying out the reaction in an heterogeneous organo-aqueous medium which is heated in the presence of a catalytic amount of a nitrogenous compound selected from the group consisting of ammonia, primary and secondary amines, and of tertiary amines and quaternary ammonium salts containing at least ten carbon atoms in the whole molecule.

It has now been determined, quite surprisingly, that the light tertiary amines described in French Pat. No. 1,357,888, such as triethylamine, while quite active when the esterification is carried out in the absence of water, are practically ineffective and are very inefficient in the presence of water, while to the contrary, other nitrogenous compounds, not used in the organic liquid phase in the absence of water, are particularly active in the process of the present invention in the presence of water, even in surprisingly low amounts.

The following more detailed description of various embodiments will provide a better understanding of the invention, it being understood that such embodiments are intended as merely exemplary and in no way limitative.

DETAILED DESCRIPTION

The halo-alkanes used in the present invention for the esterification reaction are known, and in this regard reference may be made to French Pat. No. 1,357,888. These halo-alkanes have a relatively important chemical inertia which distinguishes them from some organic halides, such as allyl chlorides or bromides, in which the halogen is activated by a neighboring group. Such halo alkanes contain from 6 to 18 carbon atoms and may be either linear or be branched, although the linear compounds are preferred since they have a higher reactivity than the corresponding branched compounds and, in addition, by further saponification, linear fatty alcohols may be synthesized therefrom. The halo-alkanes used may be either of pure or technical grades. Bromo-1-alkanes are preferred because they are inexpensive and easily obtained from an olefin and hydrobromic acid, although other halo-alkanes may also be used.

The alkali metal salt of the carboxylic acid may be introduced into the reactor preformed, in either aqueous solution or in crystallized form, or it may be itself formed in the reactor by the simple reaction between an alkali metal hydroxide, such as sodium hydroxide or potassium hydroxide, with the carboxylic acid or its corresponding anhydride. The quality of the salt is not a process critical factor and, consequently, the salt used may be either pure or of technical grade. Alkali metal salts of all the carboxylic acids react with the halo-alkanes in accordance with the present invention. Without limitation, there may be mentioned as examples the alkali-metal salts of aliphatic-mono acids such as acetic acid, of aromatic mono-acids such as benzoic acid, of aliphatic diacids such as maleic, succinic and adipic acids, and of aromatic diacids such as orthophthalic and isophthalic acids.

The relative proportions of halo-alkane and of alkali metal salt are not critical to the invention, and any proportions may be used. However, it is preferred, in order to maintain the most favorable economics, to maintain the ratio of halo-alkane mole number to carboxylate group number near 1, preferably slightly greater than 1.

The quantity of water present in the heterogeneous liquid reaction phase is also not critical to the invention. Thus, water quantity may vary within very large limits, although it is preferred that the quantity of water be maintained between 50 and 200 grams per mole of halo-alkane. The reaction proceeds with water quantities outside such range, but when the quantity of water is less than 50 grams per mole of halo-alkane the reaction speed becomes undesirably reduced; when a proportion greater than 200 grams of water per mole of halo-alkane is used, the major effect is to merely increase the volume of the reaction mass in an undesirable manner, without any increase in yield.

The selection of the catalyst is an important aspect of the present invention, and it is important not to use a tertiary amine or a quaternary ammonium salt containing less than 10 carbon atoms. However, the reaction proceeds in the presence of the water satisfactory with the use of a catalyst of ammonia, any primary or secondary amine, or any tertiary amine or quaternary ammonium salt containing in the entire molecule at least 10 carbon atoms. The catalyst is preferably chosen from compounds in which the nitrogen is not connected with a carbon belonging to an unsaturated cycle.

Among the most active catalytic compounds are the primary amines, monoethylamine and monomethylamine, the secondary amines, dimethylamine, diethylamine and morpholine, the tertiary amine, dimethyloctadecylamine, and the quaternary ammonium salt, tetrabutylammonium bromide, as examples. The quantity of catalysts necessary to obtain a quick reaction depends upon the particular catalyst selected. In general, however, the amine molar percentage with regard to the carboxylic acid alkali metal salt is generally between 0.5 and 5%. Thus, in the case of the use of light amines such as dimethyl amine, a molar percentage of 1% with regard to the alkali metal salt is quite sufficient to effect rapid reaction, such a percentage representing only 0.05% by weight of the esterification mixture. In any particular case, the optimum percentage of catalyst can be easily determined by simple calculation or by trial, it being understood that use of more or less than the optimum is permissible.

The reaction is advantageously carried out under autogeneeus pressure, although greater pressures are not excluded. The temperature is maintained between about 110° and 250°C., preferably 130° to 200°C. Within this temperature range, the optimum temperature will vary with regard to the halo-alkane chain length and the acid used, it being understood that the greater the size of the molecules of the halo-alkane and the acid, the greater the optimum temperature. It may also be desirable in some cases when using a heavier catalyst to use a slightly higher temperature.

The reaction time may vary considerably, it being understood, of course, that other things being equal, the faster the reaction time, the more favorable the economics of the reaction. In general, however, the reaction is permitted to continue for a time sufficient for the reactant present in the smallest quantity, usually the acid salt, to be transformed essentially completely into a mixture of alkyl mono and/or diesters. Usually the reaction time necessary to accomplish this result is between thirty minutes and five hours.

After the esterification, it may be desirable to saponify the formed esters in order to synthesize alcohols. This may be accomplished after removing the alkali metal halide formed during the esterification, which alkali metal halide is dissolved in the aqueous phase. Accordingly, the aqueous phase may be removed and direct saponification carried out on the organic phase. Separation of the different formed alcohols is accomplished by simple distillation.

To the contrary, where it is desired to obtain pure monoesters and/or diesters from the reaction medium in which a dicarboxylic acid alkali metal salt has been used, it is necessary to separate the reaction products such as by any convenient way known in the art. Thus, it is possible, for example, to first separate the aqueous phase containing the alkali metal halide by any convenient means such as by decantation, possibly after water dilution. Then the remaining organic phase may be washed with an aqueous solution of alkali metal or alkaline earth hydroxide, and then with water. The alkali washing will extract acid products, such as monoesters, while the water washing will bring the medium to a neutral pH. The two washings may also be carried out in the presence of a third material, such as a hydrocarbon.

Next the halo-alkane excess is removed from the organic phase in accordance with standard procedures, for example, distillation under low pressure. The distillate may be reused, and pure ester is obtained at the column bottom. The water obtained from the first washing mentioned above and containing the monoesters may be used in a second esterification reaction in accordance with the process of the present invention, the monoester molar quantity introduced in this way replacing an equivalent quantity of carboxylic acid alkali metal salt; in this way the monoesters may be converted to diesters. From the above description it will be clear that a continuous process may be easily established including recycling of excess halo-alkane and recycling of monoesters where diester only is desired.

The following examples are presented to further illustrate the invention without limitation. The first two examples emphasize the catalytic efficiency of the catalysts suggested above; comparative tests made under the same conditions show that known catalysts are not active in the presence of water.

EXAMPLE 1

With the purpose of comparing the activity of different catalysts, a series of tests was conducted consisting of reacting for 1 hour at 160°C., in an autoclave under intense stirring, a mole of sodium o-phthalate in solution in 240 g. of water with 2 moles of bromo-1-octane in the presence of 1% by mole of catalyst with regard to sodium phthalate. Table 1 below shows the transformation % of sodium phthalate in esters.

TABLE 1

| Catalyst | % of transformed phthalate |
|---|---|
| Without catalyst | 17% |
| Trimethylamine | 22% |
| Triethylamine | 22% |
| Pyridine | 21% |

TABLE 1-continued

| Catalyst | % of transformed phthalate |
| --- | --- |
| Invention: | |
| Monomethylamine | 65% |
| Dimethylamine | 80% |
| Monoethylamine | 70% |
| Diethylamine | 75% |
| Tetrabutyl ammonium bromide | 70% |

Those results emphasize clearly that light tertiary amines do not effectively catalyze the reaction under the conditions of the present process.

EXAMPLE 2

All other conditions being the same as in Example 1, the obtained results were compared by using, at the rate of 3% in mole with regard to sodium phthalate, on one hand ammonia and morpholine, and, on the other hand, a tertiary amine containing 8 carbon atoms.

TABLE 2

| Catalyst | % of transformed phthalate |
| --- | --- |
| N-butylmorpholine | 24% |
| Ammonia | 45% |
| Morpholine | 71% |

The superiority of the catalysts proposed in the present invention is emphasized again.

EXAMPLE 3

With the purpose of comparing the reactivity of different carboxylic acids, a series of tests was made, consisting of reacting, in an autoclave at 160°C., 2 moles of a carboxylic acid, 564 g. of 41% aqueous NaOH solution (quantity of alkaline hydroxide necessary for all acid salification), 1,000 g. of bromo-1-octane and 4.4 g. (0.06 mole) of N-diethylamine. Under those conditions, the time necessary for obtaining a total transformation of the alkali metal salt was determined. The results of those tests are given in the Table 3 hereinunder.

TABLE 3

| Acid | Reaction Time |
| --- | --- |
| Orthophthalic | 90 minutes |
| Isophthalic | 150 minutes |
| Adipic | 300 minutes |

EXAMPLE 4

Using the Example 3 conditions, but with a fixed reaction time of 3 hours, the quantity of N,N-dimethylamine necessary for obtaining a total transformation in the three hour period of the sodium salt of different acids was determined. The results of those series are given in Table 4.

TABLE 4

| Acid | Number of catalyst moles per acid mole |
| --- | --- |
| Acetic | 0.014 |
| Maleic | 0.030 |
| Succinic | 0.050 |

EXAMPLE 5

With the purpose of determining the influence of alkyl chain length of the halo-alkane on reactivity, 2.4 moles of bromo-1-alkane were reacted for 2.5 hours at 160°C. with an aqueous solution containing 210 g of sodium o-phthalate, 2 g. of NaOH and 236 g. of water. To obtain a total conversion of phthalate, it was necessary to use 0.45 g. of dimethylamine where the halo-alkane was bromo-1-octane, and 1.35 g. of dimethylamine where the halo-alkane was bromo-1-dodecane. With the use of bromo-1-hexadecane in the presence of 1.35 g. of dimethylamine, phthalate total conversion required maintainance of a temperature of 165°C. for 3 hours. Accordingly, it is seen that increased carbon-atom number of the halo-alkane has a small affect on the reaction, and that an increase in the reaction time, the quantity of catalyst and/or the reaction temperature compensates for increased halo-alkane chain length.

The foregoing description of specific embodiments will so fully reveal the general nature of the invention that others can, by applying current knowledge, readily modify such specific embodiments and/or adapt them for various applications without departing from the generic concept, and, therefore, such adaptations and modifications should and are intended to be comprehended within the meaning and range of equivalents of the disclosed embodiments. It is to be understood that the phraseology or terminology employed herein is for purposes of description and not of limitation.

What is claimed is:

1. In a process for the preparation of carboxylic acid alkyl esters comprising the reaction of a linear or branched 1-halo-alkane containing from 6–18 carbon atoms and an alkali metal salt of a carboxylic acid selected from the group consisting of aliphatic mono-acids and diacids and aromatic mono-acids and diacids, in the presence of a nitrogen containing catalyst, the improvement wherein:

the reaction mixture consists essentially of an heterogeneous liquid phase of the organic halo-alkane and an aqueous solution of the carboxylic acid alkali metal salt;

and wherein said reaction mixture is heated at 110°–250°C. and at least those pressures which would be generated by the reaction in a closed autoclave, said catalyst consisting essentially of a nitrogenous compound selected from the group consisting of ammonia, primary and secondary amines, and of tertiary amines and quaternary ammonium salts containing in the whole molecule at least 10 carbon atoms, said catalyst being chosen from compounds in which the nitrogen is not connected to a carbon belonging to an unsaturated cycle, and wherein said catalyst is present in a molar percentage between 0.5 and 5% with regard to said carboxylic acid alkali metal salt.

2. A process in accordance with claim 1 wherein said halo-alkane is a bromo-1-alkane containing 6 to 18 carbon atoms.

3. A process in accordance with claim 1 wherein said carboxylic acid alkali metal salt is a sodium salt of a dicarboxylic acid.

4. A process in accordance with claim 1 wherein said catalyst is selected from the group consisting of monomethylamine, dimethylamine, monoethylamine, diethylamine, morpholine, dimethyloctadecylamine and tetrabutylammonium bromide.

5. A process in accordance with claim 4 wherein said catalyst is dimethylamine or diethylamine.

6. A method in accordance with claim 1 wherein, as a preliminary operation, said carboxylic acid alkali metal salt is formed in situ by reaction in an aqueous medium of an alkali metal hydroxide with a carboxylic acid or anhydride.

7. A process in accordance with claim 1 wherein said halo-alkane is present in excess in the reaction medium, wherein the water comprising the aqueous phase is present in a quantity of between 50 and 200 grams per mole of halo-alkane, and wherein said reaction is carried out for a period of from 30 minutes to 5 hours.

8. A process in accordance with claim 1 for preparing carboxylic acid alkyl diesters, further comprising extracting the monoesters from the reaction product and recirculating said monoesters to the reaction medium to replace an equivalent molar quantity of carboxylic acid alkali metal salt.

9. A process in accordance with claim 1 wherein said catalyst is selected from the group consisting of ammonia, primary and secondary amines, and of tertiary amines containing in the whole molecule at least 10 carbon atoms, said catalyst being chosen from compounds in which the nitrogen is not connected to a carbon belonging to an unsaturated cycle.

10. A process in accordance with claim 1, wherein said reaction takes place in a closed autoclave.

* * * * *